United States Patent [19]
Landis

[11] Patent Number: 6,016,808
[45] Date of Patent: Jan. 25, 2000

[54] FACE SHIELD FRAME APPARATUS

[75] Inventor: Timothy J. Landis, Loomis, Calif.

[73] Assignee: OP-D-OP, Inc., Roseville, Calif.

[21] Appl. No.: 09/115,419

[22] Filed: Jul. 14, 1998

[51] Int. Cl.[7] .................................................. A61F 11/00
[52] U.S. Cl. .................................................. 128/857; 2/9
[58] Field of Search .................................. 128/846, 857, 128/858; 2/9, 424, 8, 15, 438, 441

[56] References Cited

U.S. PATENT DOCUMENTS

| | | |
|---|---|---|
| 2,933,734 | 4/1960 | Glass .................................................. 2/9 |
| 3,120,002 | 2/1964 | Blumenthal ...................................... 2/9 |
| 3,383,707 | 5/1968 | McNeill . |
| 3,629,870 | 12/1971 | Paisley . |
| 4,843,643 | 7/1989 | Parissenti et al. . |
| 5,016,292 | 5/1991 | Rademacher ............................. 128/858 |
| 5,468,229 | 11/1995 | Greenbaum . |
| 5,503,497 | 4/1996 | Dudley et al. . |
| 5,692,522 | 12/1997 | Landis . |

FOREIGN PATENT DOCUMENTS

| | | | |
|---|---|---|---|
| 2476332 | 8/1981 | France .......................................... 2/15 |

*Primary Examiner*—Michael A. Brown
*Attorney, Agent, or Firm*—John P. O'Banion

[57] ABSTRACT

A face shield frame apparatus having a head worn frame assembly to which a face shield can be detachably coupled. The frame assembly includes a pair of generally parallel, spaced apart side members which are joined to a front member, which is supported by the wearer's nose or forehead. One or more receptacles are provided on the frame assembly which slidably engage one or more latch arms associated with the face shield support, or conversely, the receptacle may be attached to the face shield support and the latch arm attached to the frame assembly. The latch arm has a locking tab which fits within a slot on the receptacle to lock the latch arm to the receptacle when the latch arm is inserted into the receptacle. The latch arm can also be removed from the receptacle by depressing the locking tab so that it disengages from the slot.

6 Claims, 5 Drawing Sheets

FACE SHIELD FRAME APPARATUS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to face shields and face and eye protection devices, and more particularly to a face shield apparatus having a head-worn, light-weight support frame assembly that provides for easy detachment and replacement of the face shield.

2. Description of the Background Art

Face shield devices are used in numerous professions to protect the eyes and face of wearers from various occupational hazards. Use of face shields has grown substantially in the dental and medical professions, particularly in response to the spread of AIDS and like infectious diseases, to prevent infection from body fluid splatter.

Face shields are typically supported on a wearer's head by a head band or head worn visor apparatus, with the face shield generally attached to the head band or visor such that the face shield is positioned in front of the wearer's face. In one frequently-used type of face shield device, the face shield is suspended directly from the edge or brim of a head worn visor to provide protection to a wearer's face. Other types of face shield devices provide for pivotal attachment of the face shield to the sides of a head band or visor.

A frequent problem experienced by users of face shields is that currently known face shield devices are uncomfortable to wear, particularly for extended periods of time. Wearers must frequently reposition the head band or visor which supports the face shield in order to minimize discomfort. Face shield devices which rely on head bands or head visors for support tend to cause perspiration under the band or strap, causing additional discomfort. Further, physicians, dentists, welders, and other persons who rely on face shields frequently have both hands occupied in difficult or complex procedures, and cannot free their hands to positionally adjust the face shield apparatus to reduce discomfort.

Another deficiency common to conventional face shield devices is that the face shields are not readily detachable from the devices. Face shields used in the medical and dental professions must be replaced between treatment of each patient to avoid cross-infection or cross-contamination of patients. Many currently used face shield devices do not provide for easy removal or replacement of face shields so that contaminated face shields can be sterilized or disposed.

Accordingly, there is a need for a face shield apparatus which is comfortable to wear, which is lightweight, and which provides for quick and easy detachment and re-attachment of face shields while on the wearer's head. The present invention satisfies these needs, as well as others, and generally overcomes the deficiencies found in prior devices.

BRIEF SUMMARY OF THE INVENTION

The present invention pertains to an improvement of the face shield apparatus taught in U.S. Pat. No. 5,692,522 which is incorporated herein by reference. By way of example and not of limitation, the improvement comprises a coupling means which securely attaches the face shield to the support frame assembly and allows for quick and simple one-step removal or replacement of the face shield from the support frame assembly. The coupling means generally comprises a tubular receptacle attached to the support frame assembly, a corresponding latch arm on the face shield that is slidably received by the receptacle, and a locking tab disposed on the latch arm which snaps into a slot or opening on the receptacle to latch them together. Removal of the face shield simply requires pressing down on the locking tabs while pulling the face shield away from the frame assembly. Preferably, a pair of receptacles and locking mechanisms are used, one placed at each side of the support frame assembly and face shield, respectively, although it is contemplated that one such receptacle and locking mechanism could be used by placing a crossbar between, for example, the center of the face shield and the support frame assembly. It is also contemplated that the placement of the channel members could be on the face shield bar as an alternative to placing them on the support frame assembly, in which case the latch arms would be placed on the support frame assembly.

An object of the invention is to provide a face shield apparatus having a coupling which allows for a quick and simple attachment and removal of a face shield from a support frame assembly.

Another object of the invention is to provide a face shield apparatus having a coupling means which securely locks a face shield onto a support frame assembly.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 6, where like reference numbers denote like parts. It will be appreciated that the apparatus may vary as to configuration and as to details of the parts without departing from the basic concepts as disclosed herein.

Figure 1:
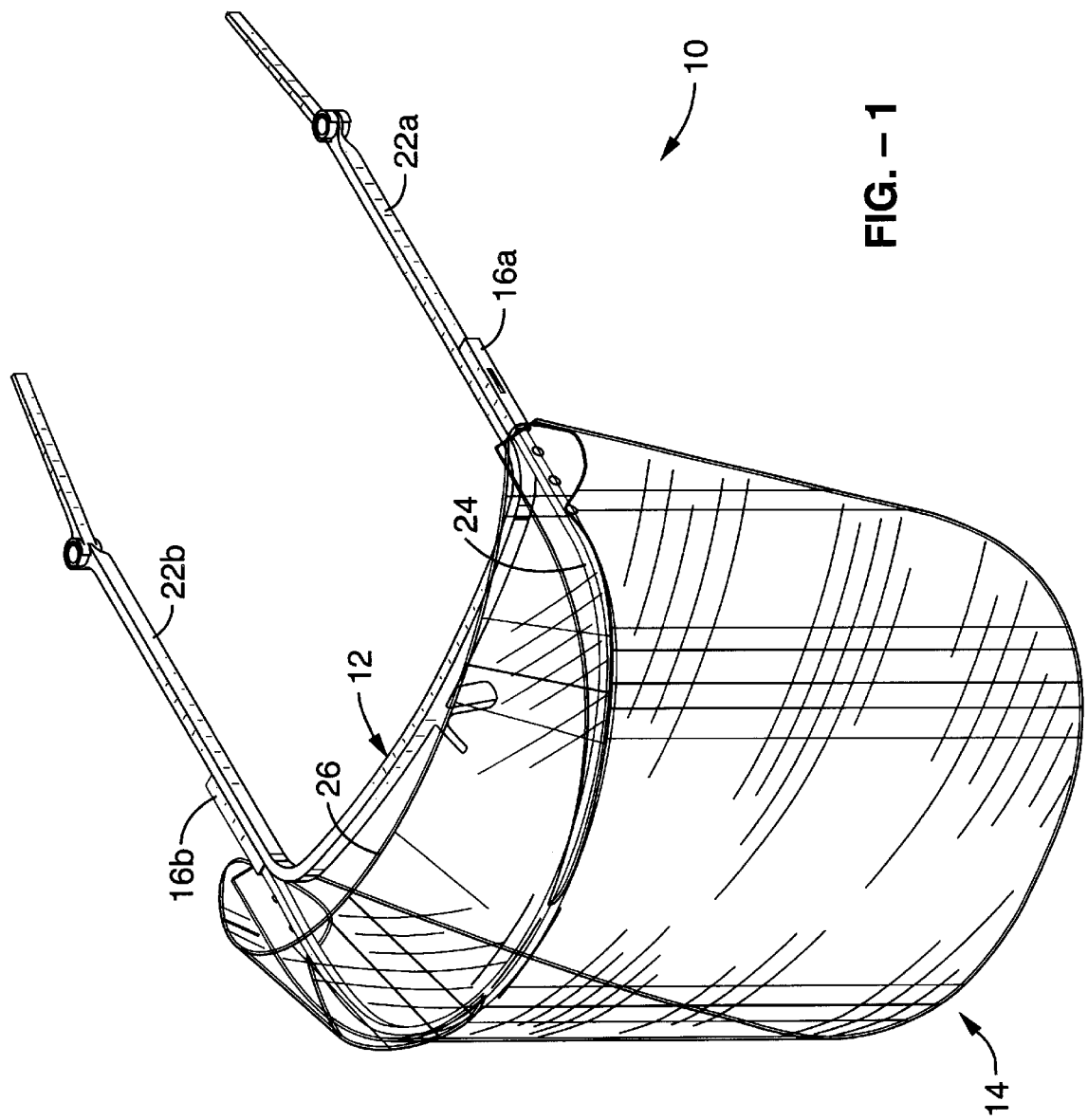
FIG. 1 is a perspective view of a face shield apparatus in accordance with the present invention.
Figure 2:
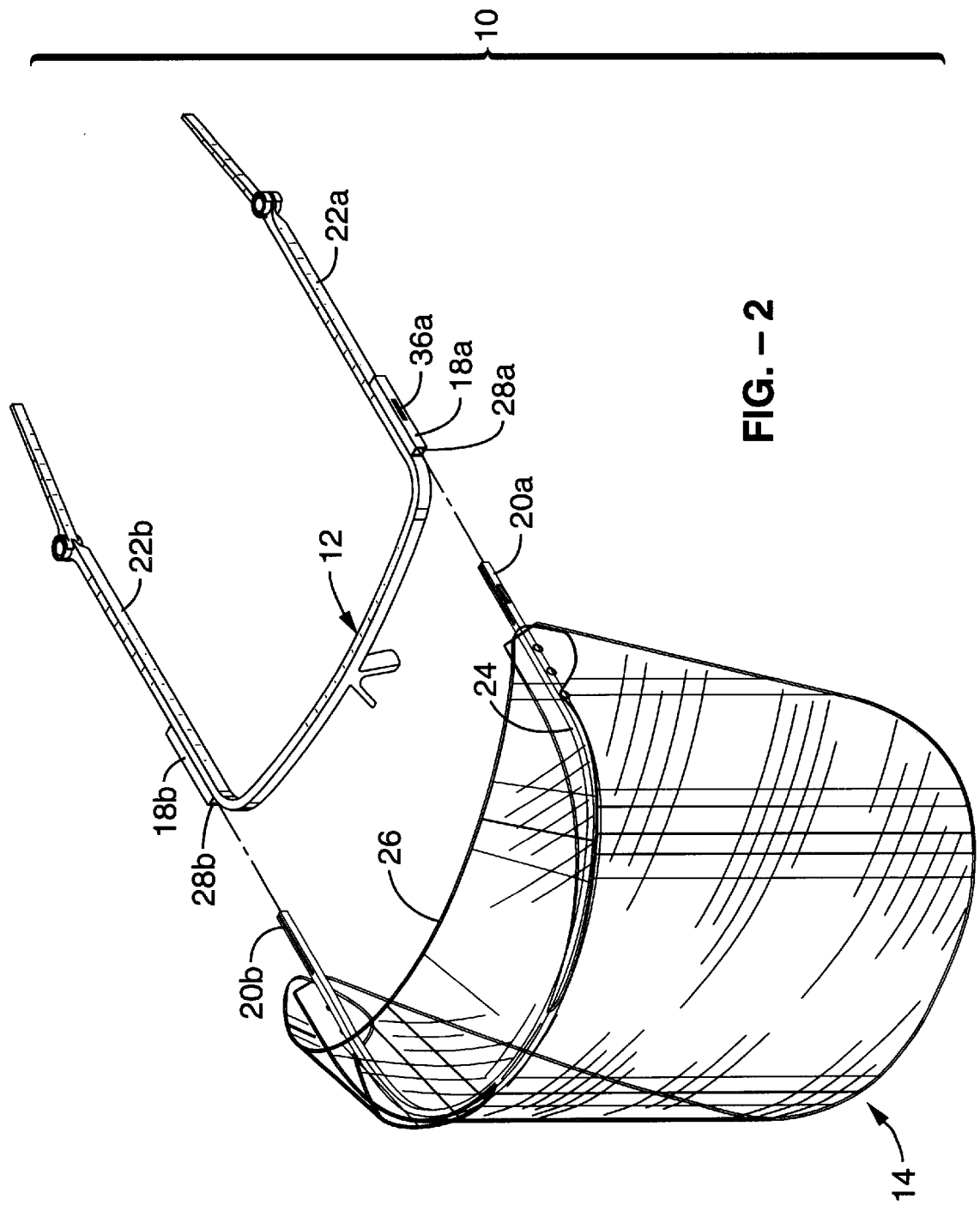
FIG. 2 is a perspective view of a face shield apparatus shown in FIG. 1 with the face shield and latch arms detached from the support frame assembly.
Figure 3:
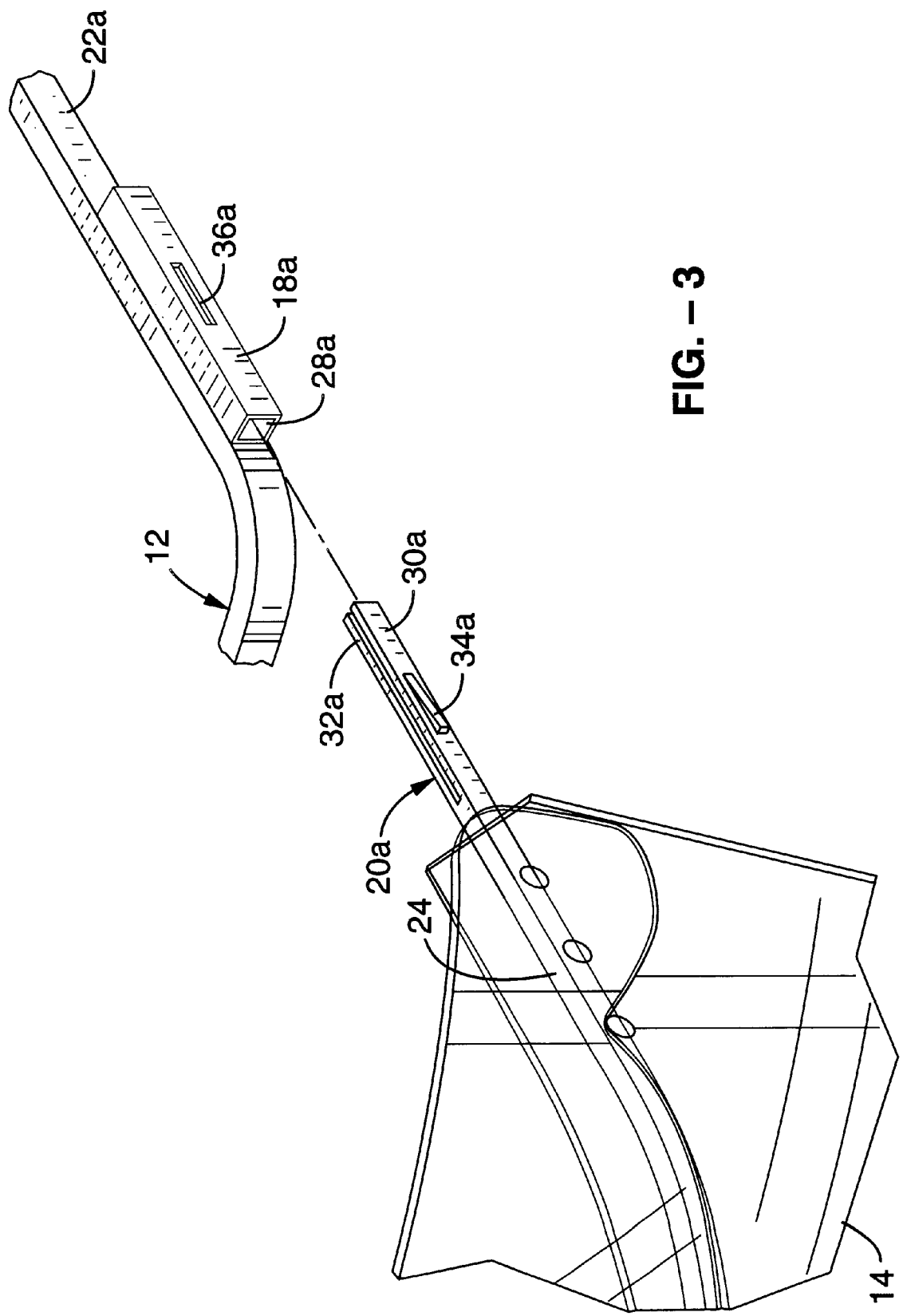
FIG. 3 is a detailed perspective view of a latch arm and channel member shown in FIG. 1.

Referring first to FIG. 1 through FIG. 3, an improved face shield apparatus 10 in accordance with the present invention is generally shown. Apparatus 10 generally includes a support frame assembly 12 and a face shield 14, as taught in U.S. Pat. No. 5,692,522 and incorporated herein by reference. Coupling means 16a, 16b provide the capability to securely attach and lock face shield 14 onto support frame assembly 12 and also provide for the quick and simple detachment and removal of face shield 14 from support frame assembly 12 when desired.

Coupling means 16a, 16b preferably comprise tubular channel members or receptacles 18a, 18b and corresponding latch arms 20a, 20b. In the preferred embodiment, receptacles 18a, 18b are permanently attached to support frame assembly 12 adjacent side members 22a, 22b, while latch arms 20a, 20b are preferably attached to and extend rearwardly from a face shield mounting bar 24. Face shield mounting bar 24 can be attached to face shield 14 in any conventional manner, including glue, tabs, pop fasteners and the like, including those described in prior U.S. Pat. No. 5,692,522. Face shield mounting bar 24 is preferably disposed adjacent the top end 26 of face shield 14 as shown. Receptacles 18a, 18b each have an opening 28a, 28b, which preferably has a square cross-section as shown, but those skilled in the art can appreciate openings 28a, 28b having other cross-sections. Receptacles 18a, 18b, along with openings 28a, 28b, are structured and configured to slidably receive latch arms 20a, 20b.

Figure 4:
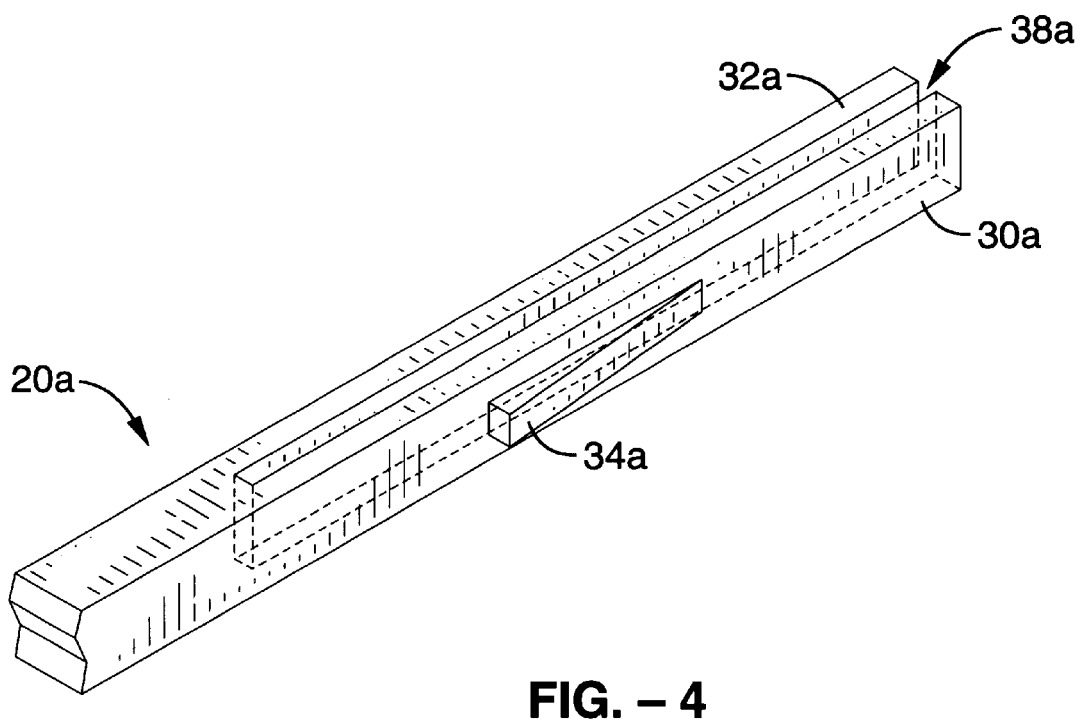
FIG. 4 is a detailed perspective view of a latch arm of the present invention.
Figure 5:
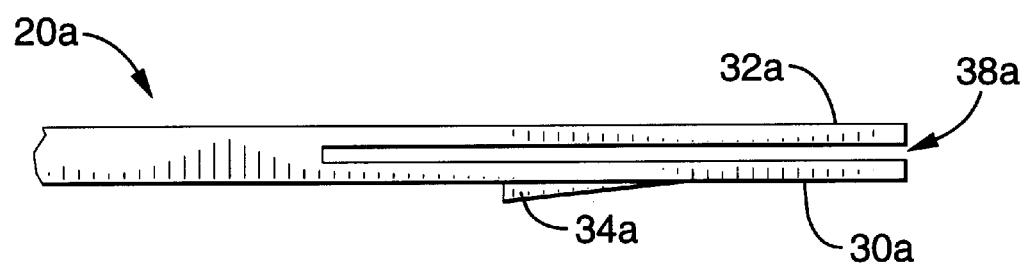
FIG. 5 is top plan view of a latch arm shown in FIG. 4.

Referring also to FIG. 4 through FIG. 5, latch arm 20a is shown in greater detail. Latch arm 20b, although not depicted in such detail, is structurally and functionally identical to latch arm 20a and, therefore, not discussed in further detail. Latch arm 20a is generally elongated and comprises a first prong 30a and a second prong 32a which are generally parallel to each other. First prong 30a and second prong 32a are structured and configured to slidably fit within opening 28a in receptacle 18a. A locking tab 34a is disposed on first prong 30a. Receptacle 18a includes an aperture or slot 36a, sized to receive locking tab 34a when arm 20a is inserted into receptacle 18a. When latch arms 20a, 20b are inserted into openings 28a, 28b of receptacles 18a, 18b, respectively, locking tabs 34a, 34b engage slots 36a, 36b as can be seen with reference to FIG. 3, thereby locking latch arms 20a, 20b in place and thus securing face shield 14 onto support frame assembly 12. To facilitate insertion of latch arm 20a into opening 28a, locking tab 34a is ramped or tapered as shown To remove face shield 14 from support frame assembly 12, locking tabs 34a, 34b must be simultaneously depressed to release them from slots 36a, 36b while latch arms 20a, 20b are withdrawn from channel members 18a, 18b. In order for locking tabs 34a, 34b to function as described, first prongs 30a, 30b (not shown) should be flexible. To accomplish this result, for example, latch arm 20a includes a gap 38a that separates first prong 30a and second prong 32a, thereby allowing first prong 30a to bend towards second prong 32a when either latch arm 20a is inserted into opening 28a or when locking tab 34a is depressed. To allow for flexibility of first prongs 30a, 30b, latch arms 20a, 20b are preferably fabricated from a resilient material, such as polystyrene, acrylic, polyethylene terephthalate, polycarbonate, or like polymeric material.

Figure 6:
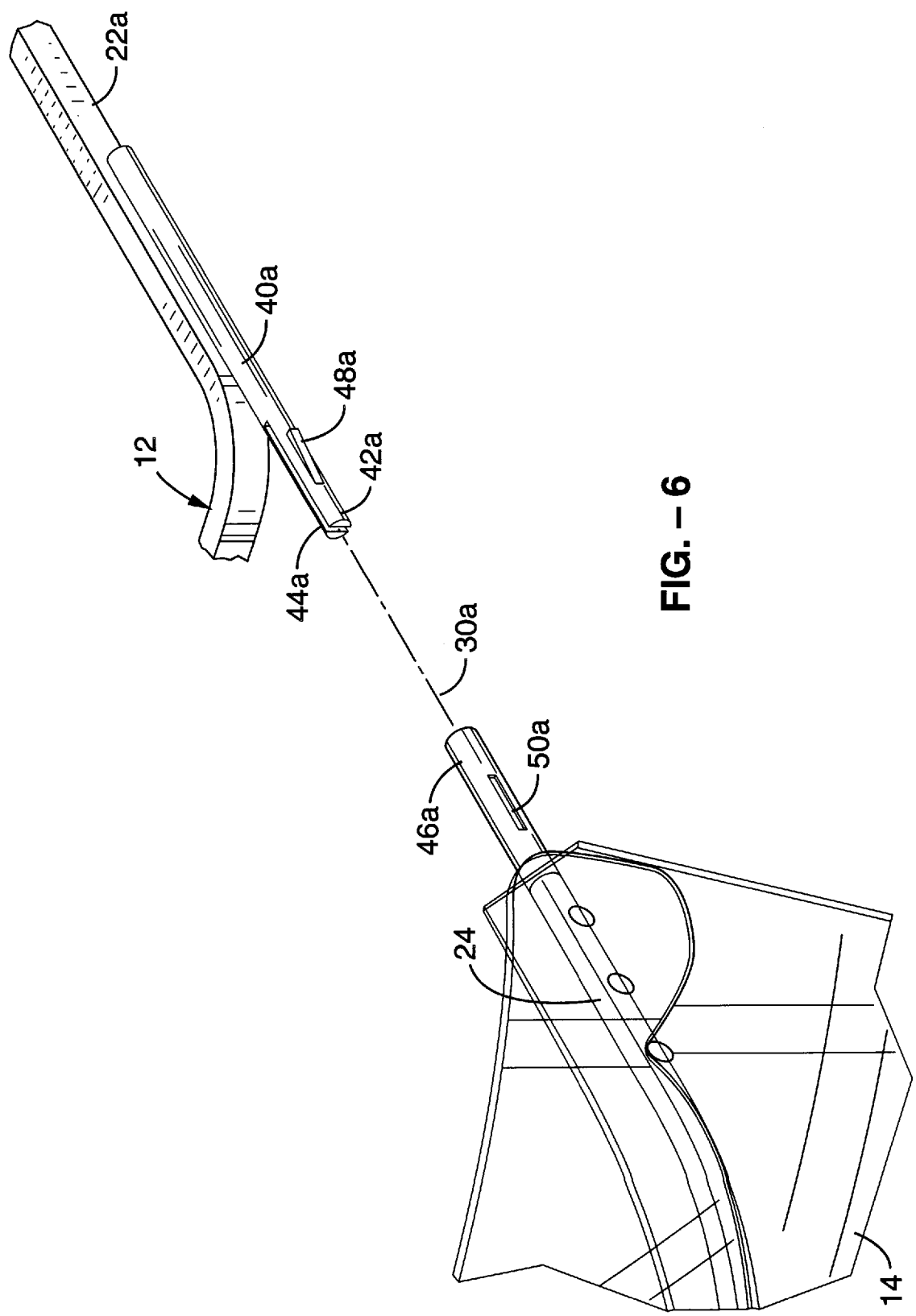
FIG. 6 is a perspective view of an alternate embodiment of the present invention.

Referring now to FIG. 6, an alternate means of attaching face shield 14 to support frame assembly 12 is shown. Here, a latch arm 40a, which has a circular cross-section, is permanently attached to side member 22a of support frame assembly 12 and extends in a forwardly direction. Latch arm 40a includes a first prong 42a and a second prong 44a, and is structured and configured to slidably engage within a receptacle 46a that is permanently attached to face shield mounting bar 24. First prong 42a includes a ramped or tapered locking tab 48a which engages slot 50a when latch arm 40a is inserted into receptacle 46a to secure face shield 14 onto support frame assembly 12.

Those skilled in the art will appreciate that various further alternative embodiments are within the scope of this invention. For example, while a pair of receptacles and latching mechanisms are preferably used, one such receptacle and latching mechanism could be used by placing a crossbar between the center of the face shield mounting bar and the support frame assembly. Furthermore, the placement of the receptacles could be on the face shield mounting bar as an alternative to placing them on the support frame assembly. In addition, the receptacles and corresponding latch arms on the face shield mounting bar could be of various cross-sections other than the square and circular cross-sections previously described such as, for example, triangular, hex, and so forth.

Accordingly, it will be seen that this invention provides a face shield apparatus which provides secure means of attaching the face shield to the support frame assembly that is easily and quickly detachable for removal and replacement of face shields. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A face shield support frame apparatus, comprising:
   (a) a head-worn support frame assembly;
   (b) a face shield mounting member; and
   (c) coupling means for coupling said face shield mounting member to said frame assembly, said coupling means having a latch arm and a receptacle configured to slidably receive said latch arm, said coupling means including locking means for latching said latch arm within said receptacle, said coupling means including release means for unlatching said latch arm from said receptacle.

2. An apparatus as recited in claim 1, wherein said coupling means further comprises:
   (a) a slot disposed on said receptacle; and
   (b) a locking tab disposed on said latch arm, said locking tab configured to engage said slot upon insertion of said latch arm into said receptacle, said locking tab configured to disengage from said slot upon depression of said locking tab.

3. A face shield support frame apparatus, comprising:
   (a) a head-worn support frame assembly;
   (b) a latch arm, said latch arm including means for coupling said latch arm to a face shield;
   (c) a receptacle coupled to said support frame assembly, wherein said receptacle is configured to slidably receive said latch arm;
   (d) locking means for latching said latch arm within said receptacle; and
   (e) release means for unlatching said latch arm from said receptacle.

4. An apparatus as recited in claim 3, further comprising:
   (a) a slot disposed on said receptacle; and
   (b) a locking tab disposed on said latch arm, said locking tab configured to engage said slot upon insertion of said support arm into said receptacle, said locking tab configured to disengage from said slot upon depression of said locking tab.

5. A face shield support frame apparatus, comprising:

(a) a head-worn support frame assembly;

(b) a latch arm coupled to said support frame assembly;

(c) a receptacle, said receptacle including means for coupling said receptacle to a face shield, wherein said receptacle is configured to slidably receive said latch arm;

(d) locking means for latching said latch arm within said receptacle; and (e) release means for unlatching said latch arm from said receptacle.

6. An apparatus as recited in claim 5, further comprising:

(a) a slot disposed on said receptacle; and (b) a locking tab disposed on said latch arm, said locking tab configured to engage said slot upon insertion of said support arm into said receptacle, said locking tab configured to disengage from said slot upon depression of said locking tab.

* * * * *